US005578475A

United States Patent [19]
Jessee

[11] Patent Number: 5,578,475
[45] Date of Patent: Nov. 26, 1996

[54] COMPOSITION AND METHODS FOR TRANSFECTING EUKARYOTIC CELLS

[75] Inventor: Joel A. Jessee, Mt. Airy, Md.

[73] Assignee: Life Technologies, Inc., Gaithersburg, Md.

[21] Appl. No.: 274,397

[22] Filed: Jul. 12, 1994

Related U.S. Application Data

[63] Continuation-in-part of Ser. No. 90,290, Jul. 12, 1993, abandoned.

[51] Int. Cl.$^6$ ............................ C12N 15/64; C12N 7/00; C12N 7/06
[52] U.S. Cl. .................... 435/172.3; 435/235.1; 435/236
[58] Field of Search ................... 435/172.3, 240.2, 435/172.1, 235.1, 236; 424/184.1, 209.1, 211.1, 218.1

[56] References Cited

U.S. PATENT DOCUMENTS 4,946,787  8/1990  Eppstein et al. .................... 435/240.2

FOREIGN PATENT DOCUMENTS

WO91/16024  10/1991  WIPO .

OTHER PUBLICATIONS

Kraaijeveld, S. A. et al., "The effect of liposomal charge on the neutralizing antibody response against inactivated encephalomyocarditis and Semliki Forest viruses," *Clin. Exp. Immunol.*, (1984) 56:509–514.
Neugebauer, J., "Detergents: An Overview," *Meth. Enzymol.*, (1990) 182:239–253.
Klappe, K. et al., "Parameters Affecting Fusion between Sendai Virus and Liposomes. Role of Viral Proteins, Liposome Composition, and pH," *Biochemistry* (1986) 25:8252–8260.
Eytan, G. D., "Use of Liposomes for Reconstitution of Biological Functions," *Biochem. Biphys. Acta* (1982) 694:185–202.
Sands, J. A., "Virucidal activity of cetyltrimethylammonium bromide below the critical micelle concentration," *FEMS Microbiol. Lett.* (1986) 36:261–263.
Walker, C. et al., "Cationic lipids direct a viral glycoprotein into the class I major histocompatibility complex antigen-presentation pathway," *Proc. Natl. Acad. Sci. USA* (1992) 89:7915–7918.
Konopka, K. et al., "Enhancement of human immunodeficiency virus type 1 infection by cationic liposomes: the role of CD4, serum and liposomes-cell interactions," *J. Gen. Virol.* (1991) 72:2685–2696.
Lapidot et al., "Fusion–Mediated MIcroinjection of Liposome–Enclosed DNA into Cultured Cells with the Aid of Influenza Virus Glycoproteins," *Experimental Cell Research* (1990) 189:241–246.

Gould–Fogerite et al., "Chimerasome–mediated gene transfer in vitro and in vivo," *Gene* (1989) 84:429–438.
Kaneda et al., "The Improved Efficient Method for Introducing Macromolecules into Cells Using HVJ (Sendai virus) Liposomes with Gangliosides," *Exp. Cell Res.* (1987) 173:56–69.
Kaneda et al., "Introduction and Expression of the Human Insulin Gene in Adult Rat Liver," *J. Biol. Chem.* (1989) 264(21):1216–1219.
Vaananen et al., "Fusion and Haemolysis of Erthrocytes caused by Three Togaviruses: Semliki Forest, Sindbis, and Rubella," *J. Gen. Virology* (1980) 46:467–475.
Young et al., "Interaction of Enveloped Viruses with Planar Bilayer Membranes: Observations on Sendai, Influenza, Vesicular Stomatitis, and Semliki Forest Viruses," *Virology* (1983) 128:186–194.
Marsh et al., "Interactions of Semliki Forest Virus Spike Glycoprotein Rosettes and Vesicles with Cultured Cells," *J. Cell. Biol.* (1983) 96:455–461.
Scheule, "Novel Preparation of Functional Sindbis Virosomes," *Biochemistry* (1986) 25:4223–4232.
Ciccarone et al., "Cationic Liposome–Mediated Transfection of Eukaryotic Cells: High Efficiency Nucleic Acid Delivery with Lipofectin, Lipofectace™, and Lipofectamine™ Regents," *FASEB J.*, Abstracts, (1993) 7(7):A1131, Abstract No. 454.
"Transfection Reagent," *Genetic Engineering News* (15 Jun. 1993) p. 12, col. 4.
Phalen et al., "Cholesterol is Required for Infection by Semliki Forest Virus," *J. Cell Biology* (1991) 112(4):615–623.
Murata et al., "Modification of the N–Terminus of Membrane Fusion–Active Peptides Blocks the Fusion Activity," *Biochem. and Biophys. Res. Communications* (1991) 179(2):1050–1055.
Schlegel, R. et al., "Biologically Active Peptides of the Vesicular Stomatitis Virus Glycoprotein," *J. Virology* 53(1):319–323.
Kamata, H. et al., "Amphiphilic Peptides Enhance the Efficiency of Liposome–mediated DNA Transfection," (1994) *Nucl. Acid Res.* 22(3):536–537.
Mazur et al., J. Am. Coll. Cardial (Feb. 10, 1993), vol. 21(2): p. 186 A.
Stegmann et al., Annu. Rev. Biophys. Biophys. Chem. (1989), vol. 18: pp. 187–211.
Grant, Hackh's Chemical Dictionary (1972), McGraw-Hill Book Company, New York, New York, p. 391.

*Primary Examiner*—George C. Elliott
*Assistant Examiner*—Terry A. McKelvey
*Attorney, Agent, or Firm*—Greenlee, Winner and Sullivan, P.C.

[57] ABSTRACT

The present invention provides compositions and methods for transfecting eukaryotic cells which comprises a nucleic acid, a cationic lipid capable of forming a complex with said nucleic acid, and a viral agent which is an active or inactive enveloped virus or a component of an enveloped virus.

36 Claims, No Drawings

COMPOSITION AND METHODS FOR TRANSFECTING EUKARYOTIC CELLS

RELATED APPLICATION

This application is a continuation-in-part of U.S. patent application Ser. No. 08/090,290, filed Jul. 12, 1993, now abandoned, which is incorporated by reference in its entirety herein.

FIELD OF THE INVENTION

Compositions of cationic lipids and viral components useful for transfecting eukaryotic cells with nucleic acids and for introduction of other macromolecules into such cells are disclosed. Also disclosed are methods of transfecting eukaryotic cells employing such compositions.

BACKGROUND OF THE INVENTION

Lipid aggregates such as liposomes can function to facilitate introduction of macromolecules, such as DNA, RNA, and proteins, into living cells. Recently, it has been shown that lipid aggregates comprising cationic lipid components can be especially effective for delivery and introduction of large anionic molecules, such as nucleic acids, into certain types of cells. See Felgner, P. L. and Ringold, G. M. (1989) Nature 337:387–388. Since the membranes of most cells have a net negative charge, anionic molecules, particularly those of high molecular weight, are not readily taken up by cells. Cationic lipids aggregate to and bind polyanions, such as nucleic acids, tending to neutralize the negative charge. The effectiveness of cationic lipids in transfection of nucleic acids into cells is thought to result from an enhanced affinity of cationic lipid-nucleic acid aggregates for cells.

A variety of types of lipid aggregates are known, including liposomes, unilamellar vesicles, multilamellar vesicles, micelles and the like, having particle sizes in the nanometer to micrometer range. As is well-known in the art, the structures of lipid aggregates depend on the lipid composition and the method employed to form the aggregate. Cationic lipids can be used alone or in combination with non-cationic lipids, for example with neutral phospholipids like phosphotidylethanolamines, to form positively charged vesicles and other lipid aggregates which are able to bind nucleic acids. The positively charged lipid aggregates bind to nucleic acids, can then be taken up by target cells and thus facilitate transfection of the target cells with the nucleic acid. (See, Felgner, P. L. et al. (1987) Proc. Natl. Acad. Sci. USA 84:7413–7417; Epstein, D. et al. U.S. Pat. No. 4,897,355.)

Cationic lipids are not universally effective for transfection of all cell types. Effectiveness of transfection of different cells depends on the cationic lipid composition used and the type of lipid aggregate formed. In addition, a particular cationic lipid may be more or less toxic to a given cell line, limiting the type or concentration of lipid that can be employed for transfection. Certain types of higher eukaryotic cells are not readily transfected employing presently available cationic lipids. These hard to transfect cells generally include suspension cell lines and primary human cell lines and more specifically include fibroblasts and macrophage cell lines. Compositions and methods which would generally enhance the efficiency of cationic lipid-mediated transfection and/or broaden the range of cell types that can be efficiently transfected with cationic lipid-DNA complexes would represent valuable improvements in the art.

Many biological materials are taken up by cells by receptor-mediated endocytosis. See: Pastan and Willingham (1981) Science 214:504–509. This mechanism involves binding of a ligand to a cell-surface receptor, clustering of ligand-bound receptors, and formation of coated pits followed by internalization of the ligands into endosomes. Both enveloped viruses, like influenza virus and alphaviruses, and non-enveloped viruses, like adenovirus, infect cells via endocytotic mechanisms. See: Pastan, I. et al. (1986) in *Virus Attachment and Entry into Cells*, (Crowell, R. L. and Lonberg-Holm, K., eds.) Am. Soc. Microbiology, Washington, p. 141–146; Kielian, M. and Helenius, A. (1986) "Entry of Alphaviruses" in *The Togaviridae and Flaviviridae*, (Schlesinger, S. and Schlesinger, M. J., eds.) Plenum Press, New York p. 91–119; FitzGerald, D. J. P. et al. (1983) Cell 32:607–617. Receptor-mediated endocytosis has been exploited to deliver DNA into cells. Wu, G. Y. and Wu, C. H. (1987) J. Biol. Chem. 262:4429–4432; Wagner, E. et al. (1990) Proc. Natl. Acad. Sci. USA 87:3410–3414. These methods employ bifunctional conjugates having a ligand, which binds to a specific cell-surface receptor, covalently linked to a DNA-binding domain. Asialoglycoprotein-polylysine conjugates and human transferrin-polylysine conjugates have, for example, been demonstrated to mediate DNA entry into certain eukaryotic cells. (Wagner, E. et al., 1990, supra).

Curiel, D. T. et al. (1991) Proc. Natl. Acad. Sci. USA 88:8850–8854 and Cotton, M. et al. (1992) Proc. Natl. Acad. Sci. USA 89:6094–6098 have recently reported that receptor-mediated transfection via transferrin-polylysine/DNA complexes is enhanced by simultaneously exposing the cells to defective adenovirus particles. These authors report that adenovirus particles function to disrupt endosomes containing the viral particle and the DNA complex. Replication-defective adenovirus particles and psoralen inactivated adenovirus were reported to enhance transfection. Adenovirus enhancement of transfection is limited, however, to cells which have both a ligand receptor, i.e. transferrin receptor, and an adenovirus receptor. Direct coupling of polylysine/DNA complexes to adenoviruses has also been employed for transfection. Curiel, D. T. et al. (1992) Hum. Gene Therapy 3:147–154; Wagner, E. et al. (1992) Proc. Natl. Acad. Sci. USA 89:6099–6103. In related work, Wagner, E. et al. (1992) Proc. Natl. Acad. Sci. USA 89:7934–7938, report augmentation of transfection in several cell lines when hemagglutinin HA-2 N-terminal fusogenic peptides from influenza virus are included in transferrin-polylysine-DNA complexes. The use of influenza peptide conjugates was, however, reported to be less effective for enhancement of transfection than defective adenovirus.

PCT patent applications WO 93/07283 and WO 93/07282, both published Apr. 15, 1993, relate to transfection of higher eukaryotic cells via ligand/polylysine/DNA complexes and endosomolytic agents, such as adenovirus and HA-2 fusogenic peptides.

Alphaviruses, mosquito-transmitted members of the family Togaviridae, are RNA-containing enveloped viruses (also called membrane viruses). Alphaviruses include, among others, Sindbis and Semliki Forest (SFV) viruses, several equine encephalitis viruses (Eastern (EEE), Western (WEE) and Venezuelan (VEE)), Chikungunya virus and Ross River virus. Sindbis and Semliki Forest viruses are the least virulent and best characterized alphaviruses. See generally: Schlesinger, S. and Schlesinger, M.J., eds. (1986) The Togaviridae and Flaviviridae, Plenum Press. Alphaviruses in general, and specifically SFV and Sindbis virus, have very broad host ranges. SFV infects a wide variety of cultured cells including mammalian (human, monkey, hamster, mouse, porcine), avian, reptilian, amphibian and insect cell lines. Liljestrom P. and Garoff, H. (1991) Biotechnology 9:1356–1361 and references cited therein. Animal cell expression vectors have been based on SFV (Liljestrom and Garoff (1991), supra) and Sindbis virus (Xiong, C. et al. (1989) Science 243:1188–1191). The entry of alphaviruses into cells has been studied using SFV as a model. Kielian and Helenius (1986) supra. As with other viruses, SFV binds to the cell membrane, and is internalized in coated vesicles. In contrast to non-enveloped viruses, SFV (and other enveloped viruses) is released into the cell cytoplasm by fusion of the viral envelope with the endosome membrane. Acidic pH triggers the fusion process. The fusion process in SFV is characterized as rapid, non-leaky and strictly dependent, both in in vitro fusion with liposomes and in vivo infection, on the presence of a 3β-OH sterol, such as cholesterol, in the membrane to which the virus fuses. Kielian, M. and Helenius, A. (1985) J. Cell Biol. 101:2284–2291; Kielian, M. and Helenius, A. (1984) J. Virol. 52:281–283; White, J. and Helenius, A. (1980) Proc. Natl. Acad. Sci. USA 77:3273–3277; Phalen, T. and Kielian, M. (1991) J. Cell. Biol. 112:615–623. Although the detailed mechanism of fusion in alphaviruses (SFV and Sindbis virus) is not completely understood, alphavirus fusion is reported to be distinct from that of influenza virus. Kielian and Helenius (1985) supra; Wahlberg J. M. et al. (1992) J. Virol. 66:7309–7318. As noted above, fusion of the influenza virus is associated with influenza hemagglutinin (HA). An acidic pH-induced conformational change in HA exposes a hydrophobic domain, containing N-terminal sequences of the HA-2 subunits, which is thought to bind to the target membrane facilitating fusion. SFV spike glycoprotein is distinct in size, structure and amino acid sequence from HA and does not have a hydrophobic domain linked to fusion as does HA.

In addition to the togaviruses (e.g., alphaviruses) and orthomyxoviruses (influenza), enveloped viruses include the following major families of animal viruses: Herpesviridae, Bunyaviridae, Paramyxoviridae, Rhabdoviridae, Retroviridae, Arenaviridae, Coronaviridae and some members of Iridoviridae. Although all enveloped viruses are released into the cell cytoplasm by fusion of the viral envelope with the outer cell membrane, the specific fusagenic component and thus mechanism of fusion may vary. For example, vesicular stomatitis virus (VSV), a rhabdovirus, infects host cells via adsorptive endocytosis. See, e.g., Dahlberg, J. E. (1974) Virology 58:250–262; Dickson, R. B. et al. (1981) J. Cell Biol. 89:29–34; Fan, D. and Sefton, B. (1978) Cell 15:985–992; and Matlin, K. S. et al. (1982) J. Mol. Biol. 156:609–631. VSV fusion is thought to involve interaction between the VSV glycoprotein (G protein) and specific membrane lipids (Schlegel, R. et al. (1983) Cell 32:639–646). The VSV G protein reportedly binds preferentially to "saturable receptors" such as acidic phospholipid phosphatidylserine (Schlegel, R. and Wade, M. (1985) J. Virol. 53(1):319–323. Unlike the fusion process for SFV, VSV fusion does not require the presence of a 3β-OH sterol. See: Young, J. D. E. et al. (1983) Virology 128:186–194, and Phalen, T. and Kielian, M. (1991) supra.

The present invention is based on the discovery that components of enveloped viruses can significantly enhance the efficiency of cationic lipid-mediated transfection of eukaryotic cells. Unlike prior art methods, the enhanced transfection methods of this invention do not require encapsulation of the nucleic acid within anionic phospholipid-based liposomes. The present invention thus eliminates the need to construct liposomes for each particular nucleic acid, an inconvenient and often difficult procedure. Moreover, the enhanced transfection methods of this invention do not require conjugation of a polycation to a ligand, nor to the virus itself. The methods of this invention are applicable to a wider range of cell-types than prior art methods. There is no requirement for specific ligand receptors in target cell lines. Furthermore, since the alphaviruses, at least SFV, require only cholesterol or closely related sterols in target cells, the range of cells to which the methods of this invention can be applied is much broader than prior art methods. In addition, the methods of this invention can be combined with techniques well-known in the art for introducing cholesterol into cell membranes or enhancing the level of cholesterol in cell membranes to further enhance transfection efficiency or further broaden the range of cell types to which these methods are applicable.

SUMMARY OF THE INVENTION

The present invention provides compositions and methods for transfecting eukaryotic cells, particularly higher eukaryotic cells, with nucleic acids. Nucleic acids, both DNA and RNA, are introduced into cells such that they retain their biological function. A composition for transfecting eukaryotic cells comprising a cationic lipid and an enveloped virus or a component of an enveloped virus is provided. Transfecting compositions comprise cationic lipid which functions, alone or optionally in combination with non-cationic lipid, to form cationic lipid aggregates which complex nucleic acids. Cationic lipid aggregates, including liposomes, vesicles and micelles, facilitate introduction of anionic macromolecules, like nucleic acids, through cell membranes which are typically negatively charged.

Transfecting compositions also comprise an active or inactive enveloped virus capable of entry into the eukaryotic cell to be transfected or a viral component of an enveloped virus that functions to facilitate entry of cationic lipid aggregates into that cell. Viral components of enveloped viruses useful in transfection compositions include viral proteins, particular viral spike glycoproteins, multimers (i.e, dimers and trimers) thereof, viral peptides of viral spike glycoproteins, and viral envelope fragments containing embedded viral protein. Because of their very broad host range, alphaviruses are preferred for transfection. Preferred alphaviruses are Semliki Forest virus and Sindbis virus. Transfecting compositions comprising viral components of influenza virus or vesicular stomatitis virus are also preferred.

Inclusion of an enveloped virus in a transfection composition with cationic lipid aggregates complexed with nucleic acids significantly enhances transfection (2-fold or more) compared to transfection mediated by the cationic lipid alone. Enhancement of transfection by enveloped viruses, such as togaviruses, rhabdoviruses and orthomyxoviruses, is pronounced in cell lines, including suspension cell lines, animal primary cell lines, and human primary cell lines, that have been found to be hard to transfect employing prior art cationic lipid-mediated transfection methods. Enhancement of transfection by enveloped viruses occurs in any cell which the virus can enter and infect. Enhancement of transfection with alphaviruses, particularly SFV, occurs in cells which comprise cholesterol or another 3βOH-sterol in their cell membrane. Enhancement of transfection by vesicular stomatitis virus occurs with a wide range of cells, particularly cells which contain "saturable receptors" such as acidic phospholipid phosphatidylserine.

Monovalent or preferably polyvalent cationic lipids are employed in transfecting compositions. Preferred polyvalent cationic lipids are lipospermines, specifically DOSPA (2,3-droleylocy-N-[2(sperminecarboxamido)ethyl]-N,N-dimethyl-1-propanaminium trifluoroacetate). Cationic lipids are optionally combined with non-cationic lipids, particularly neutral lipids, for example lipids such as DOPE (dioleoylphosphatidylethanolamine). A cationic lipid composition composed of a 3:1 (w/w) mixture of DOSPA and DOPE is generally useful in transfecting compositions of this invention. Cationic lipid aggregates can also include 3βOH-sterols, particularly cholesterol. Cationic lipid aggregates that contain 3βOH sterol are particularly useful in combination with alphaviruses. Transfection compositions also optionally contain agents which inhibit lysosomal enzymes or enhance release of material from endosomes, such as chloroquine. Preferred transfection compositions are those which induce substantial transfection of a higher eukaryotic cell line. Substantial transfection is the introduction of functional nucleic acid in 50% or more of the cells in a transfection sample.

The methods of the present invention involve contacting a eukaryotic cell with a transfecting composition containing a cationic lipid, an active or inactive envelope virus or a viral component of such a virus, and a nucleic acid. A preferred method employs an active or inactive alphavirus or a viral component of an alphavirus. Methods employing alphavirus, particularly Semliki Forest virus, are widely applicable to transfection of eukaryotic cell types having cell membranes that contain cholesterol or other 3βOH-sterols. Methods employing rhabdoviruses, particularly vesicular stomatitis virus, are widely applicable to transfection of eukaryotic cell types having cell membranes that contain saturable "receptors" such as phosphatidylserine. Methods of this invention are applicable to transfection of adherent or suspension cell lines, in general to animal cell lines, specifically to mammalian, avian, reptilian, amphibian and insect cell lines and more specifically to animal primary cell lines, human primary cell lines, stem cell lines, and fibroblasts. These methods generally enhance transfection of hard to transfect cell lines.

The lipids, viruses, and nucleic acid of transfecting compositions can be combined in a variety of ways prior to contact with cells.

In one alternative transfection method, cationic lipid aggregates are formed and complexed with nucleic acid. Virus or viral component is then added to the nucleic acid complexes and the resulting mixture is employed to transfect cells.

In a second alternative transfection method, cationic lipid aggregates are formed and viral components are incorporated into the cationic lipid aggregate, the resulting aggregate is complexed with nucleic acid and the resulting nucleic acid complexes are employed to transfect cells. Viral components can be incorporated into the lipid aggregate, for example by application of a freeze-thaw cycle to a mixture containing lipid and virus.

In a third alternative transfection method, cationic lipid aggregates are complexed with nucleic acid, viral components are incorporated into the nucleic acid/cationic lipid complexes and the resulting complexes are employed to transfect cells.

In each of these alternative methods, cationic lipid aggregates can contain non-cationic lipids and 3β-OH sterols, like cholesterol. In each of these alternative methods, agents which inhibit lysosomal enzymes or enhance release of material from endosomes, such as chloroquine can be added to the transfecting composition.

Transfection methods of this invention employing alphavirus can be further improved by adding a step introducing a 3βOH-sterol, preferably cholesterol, into the cell membrane of the target cell to be transfected. The 3βOH sterol can be introduced into a target cell that contains no 3βOH sterol, making the 3βOH sterol-treated cell susceptible to alphavirus entry. Alternatively, the level of 3βOH sterol in a target cell can be increased to enhance transfection of nucleic acids into the cell in the presence of alphavirus and cationic lipid. Semliki Forest virus are particularly useful in such methods. Cholesterol and other 3βOH-sterols can be introduced into cell membranes prior to or simultaneous with the step of contacting the cell with the transfecting composition. Cells can be pretreated, for example, by growth on medium containing high levels of cholesterol or other 3βOH-sterol. Alternatively, liposome fusion or exchange techniques can be employed to introduce desired 3βOH-sterols. Cholesterol or another 3βOH-sterol can also be incorporated into the cationic lipid aggregates in the transfecting composition. Transfection of eukaryotic cells is enhanced when 3βOH sterol-containing cationic lipid aggregates are combined with alphaviruses and nucleic acids and used to transfect those cells.

The transfection methods of the present invention can be applied to in vitro and in vivo transfection of eukaryotic cells, particularly to transfection of higher eukaryotic cells including animal cells. The methods of this invention can be used to generate transfected cells which express useful gene products. The methods of this invention can also be employed as a step in the production of transgenic animals. The methods of this invention are useful as a step in any therapeutic method requiring introducing of nucleic acids into cells. In particular, these methods are useful in cancer treatment, in in vivo and ex vivo gene therapy, and in diagnostic methods. The transfection compositions of this invention can be employed as research reagents in any transfection of eukaryotic cells done for research purposes. Nucleic acids that can be transfected by the methods of this invention include DNA and RNA from any source comprising natural bases or non-natural bases, and include those encoding and capable of expressing therapeutic or otherwise useful proteins in cell, those which inhibit undesired expression of nucleic acids in cell, those which inhibit undesired enzymatic activity or activate desired enzymes, those which catalyze reactions (Ribozymes), and those which function in diagnostic assays.

The compositions and methods provided herein can also be readily adapted in view of the disclosure herein to introduce biologically-active anionic macromolecules other than nucleic acids including, among others, polyamines, polyamine acids, polypeptides, proteins, biotin, and polysaccharides into eukaryotic cells. Other materials useful, for example as therapeutic agents, diagnostic materials, research reagents, which can be complexed by the cationic lipid aggregates and introduced into eukaryotic cells by the methods of this invention.

DETAILED DESCRIPTION OF THE INVENTION

The present invention provides improved methods for transfecting eukaryotic cells with nucleic acid employing cationic lipids. The improvement relates to the use of an enveloped virus or a component of an enveloped virus to either enhance the efficiency of transfection or to broaden the range of types of cells that can be transfected. This invention has significant advantages over prior art methods of transfection which employ viruses. There is no limit on the size or composition of nucleic acid that can be transfected and there is no requirement for chemical modification of the nucleic acid. The method does not require the use of a ligand that binds to cell-surface receptors and nucleic acid-complexing agents need not be chemically linked to such ligands nor to viral particles. The methods are useful for transfection of a wider range of cell types than prior art methods. Methods of this invention employing alphaviruses, especially Semliki Forest virus, are applicable to a wide range of higher eukaryotic cells, both vertebrate and invertebrate, including but not limited to mammalian, avian, reptilian, amphibian and insect cells. The range of cell types that can be transfected by the methods of this invention can be further expanded by introducing a 3βOH-sterol, particularly cholesterol, into the cell membrane of a cell to be transfected.

The following definitions are employed in the specification and claims.

Lipid aggregate is a generic term that includes liposomes of all types both unilamellar and multilamellar as well as vesicles, micelles and more amorphous aggregates. A cationic lipid aggregate is a lipid aggregate comprising sufficient cationic lipid, optionally in combination with non-cationic lipids, such that the lipid aggregate has a net positive charge. Cationic lipids and lipid aggregates of this invention are capable of complexing with nucleic acids.

The term transfection is used herein generally to mean the delivery and introduction of biologically functional nucleic acid into a cell, i.e. a eukaryotic cell, in such a way that the nucleic acid retains its function within the cell. The term transfection includes the more specific meaning of delivery and introduction of expressible nucleic acid into a cell such that the cell is rendered capable of expressing that nucleic acid. The term expression means any manifestation of the functional presence of the nucleic acid within a cell, including both transient expression and stable expression. Nucleic acids include both DNA and RNA without size limits from any source comprising natural and non-natural bases. Nucleic acids can have a variety of biological functions. They may encode proteins, comprise regulatory regions, function as inhibitors of gene or RNA expression (e.g., antisense DNA or RNA), function as inhibitors of proteins, function to inhibit cell growth or kill cells, catalyze reactions or function in a diagnostic or other analytical assay.

The transfection methods of this invention employing cationic lipids in combination with alphaviruses can display significant enhancement of transfection (2-fold or more) over transfection methods employing comparable cationic lipids alone. Preferred transfection compositions and methods of this invention are those that result in transfection of 50% or more of the cells in a cell sample contacted with the transfection composition.

Transfection activity or efficiency is measured by detecting the presence of the transfected nucleic acid in a cell. This is often assessed by measuring the biological function of the nucleic acid in the cell, and most often assessed by measuring the level of transient or stable expression of a reporter gene comprised in the transfected nucleic acid. Reporter gene expression depends among other things on the amount of nucleic acid transfected as well as promoter function in the cell. Transfection activity can also be assessed by determining the percent of cells in a sample that have been transfected, for example, by assessing reporter gene expression using cell counting methods.

The methods of the present invention are particularly useful for transfection of cells that have been found to be hard to transfect employing prior art cationic lipid methods, for example the use of cationic lipid reagents like "LIPOFECTAMINE". The term "hard to transfect" refers to those eukaryotic cell lines in which, under transfection assay conditions as described in Example 3, less than about 10% of the cells in a sample are transfected employing the cationic lipid reagent "LIPOFECTAMINE". Hard to transfect cells include animal primary cell lines including human fibroblasts, animal embryo stem line cells, keratinocytes and macrophage. Other hard to transfect cell lines can be identified employing assay conditions as described in Example 3.

The method of this invention involves contacting a eukaryotic cell with a transfection composition comprising a cationic lipid, a virus or viral component and a nucleic acid. The transfection composition optionally comprises a non-cationic lipid, preferably a neutral lipid. The virus or viral component is an enveloped virus or a component thereof and is preferably an alphavirus, an influenza virus or a vesicular stomatitis virus or a component thereof. Enhanced transfection methods of this invention have been demonstrated with the prototype alphavirus Semliki Forest virus and the prototype fusagenic peptides from influenza virus (E5 amphiphilic peptide) and vesicular stomatitis virus (G protein).

The cationic lipid, alone or in combination with a non-cationic lipid, forms a cationic lipid aggregate which can bind nucleic acid. A cationic lipid aggregate may form spontaneously in an appropriate medium or various well-known techniques may be employed to produce a desired type of lipid aggregate. In particular, well-known techniques may be applied to form cationic liposome or vesicles. The relative amounts of cationic lipid and non-cationic lipid employed to form the lipid aggregate depends on the type of aggregate desired, the toxicity of the lipids to the cell and the environment (e.g. medium) in which the aggregate is to be employed. The kinds and amounts of lipids employed are typically balanced to minimize cell toxicity and maximize transfection efficiency. The cationic lipid aggregate complexes the nucleic acid that is to be transfected into cells. Nucleic acid complexes can be formed by combining nucleic acids with lipid prior to aggregate formation or by adding nucleic acid to already-formed cationic lipid aggregates. Nucleic acids can, for example, be complexed to the outer surface of cationic liposomes or vesicles. Alternatively, nucleic acids can be included within liposomes or vesicles. Transfecting compositions of this invention may contain a mixture of structurally distinct cationic lipid aggregates.

Alternative methods of combining cationic lipid, neutral lipid, virus or viral component and nucleic acid can be used in the methods of this invention. For example, transfecting compositions include, but are not limited to, those in which:

cationic lipid aggregates are formed, complexed with nucleic acid and the resulting complexes are combined with virus or viral components;

cationic lipid aggregates such as liposomes are formed, the aggregates are fused with virus, the resulting virus-fused aggregates are complexed with nucleic acids;

cationic lipid, neutral lipid and virus or viral components are combined and subjected to treatments to form lipid aggregates and the resulting aggregates are complexed with nucleic acid; or cationic lipid, neutral lipid virus or viral component and nucleic acid are combined and subjected to treatments to form lipid aggregates.

Transfection compositions contain active or inactive enveloped virus or components thereof. The virus can include wild-type or mutant virus, so long as the mutant virus remains capable of entering a cell. Wild-type virus is generally not preferred due to safety concerns. The use of replication-deficient virus and virus inactivated by various methods is preferred. The terms inactive virus is used herein to refer to a virus which, after exposure to certain chemical or physical conditions, is no longer capable of expressing its viral RNA. Inactivation of SFV is assessed herein by exposing viral particles whose RNA contains a reporter gene under the control of the viral subgenomic promoter to potentially inactivating conditions. Cells (BHK-21 cells) infected with the exposed viral particles are then assayed for reporter gene expression. Cells infected with inactive virus display no expression of reporter gene. Viruses that are incapable of secondary infection are also useful in the methods of this invention. Infectious SF particles incapable of secondary infection because the structural protein region has been deleted from their RNA can be formed as described in Liljestrom and Garoff (1991) Biotechnology 9:1356. Such SF particles can enter cells, but are incapable of producing infectious virus particles after entry into cells. Similar methods can be employed to produce Sindbis particles incapable of secondary infection (Xiong, C. et al. (1989) Science 243:1188–1191) and can be readily adapted to other alphaviruses.

Inactive virus useful in this invention can be prepared by a variety of methods. UV-inactivation, heat-inactivation and disruption of virus by application of freeze-thaw cycles can be employed. Inactivation conditions can be readily optimized for different virus and to obtain inactivation without affecting the ability of the virus to enter cells.

Viral components can also be employed in the methods of this invention. Useful viral components are those components, membrane fragments, spike glycoproteins, multimers of spike glycoproteins (dimers and trimers) and peptides of spike glycoproteins that function to enhance transfection of cationic lipid aggregate/nucleic acid complexes into cells. Viral proteins, multimers of viral proteins and peptides of viral proteins can be incorporated into cationic lipid aggregates to achieve enhanced transfection. Viral components can be isolated by a variety of well-known techniques, for example using the cationic detergent DTAB as described in Glushakova, S. E., et al. (1985) "Influenza viral glycoproteins isolation using cationic detergent dodecylmethylammonium bromide and its subsequent integration into liposomal membrane" Mol. Genet. Mikrobiol. Virol. 4:39–44. Alternatively, viral components can be produced by a variety of standard chemical syntheses methods. Viral fusagenic peptides, for example, can be synthesized using automated solid phase peptide synthesis as described, e.g., in Stewart et al. (1984) Solid Phase Peptide Synthesis, Pierce Chemical Company, Rockford, Ill. Fusagenic peptides from influenza and vesicular stomatitis virus, including the exemplified E5 amphiphilic peptide and G protein, are particularly useful in the methods of this invention.

Cationic lipid aggregates which comprise viral components, such as viral envelope fragments containing spike glycoprotein, can be produced by a variety of well-known techniques. For example, methods such as those described for the preparation of proteoliposomes, virasomes and chimerasomes can be employed or readily adapted. Gould-Fogerite, S. et al. (1989) Gene 84:429–438; Marsh, M. et al. (1983) J. Cell Biol. 96:455–461; Tikchonenko, T. I. et al. (1988) Gene 63:321–330.

Media employed in transfections should preferably be free of components, like serum or high salt levels, that can inhibit cationic lipid-mediated transfection of cells or that can inhibit entry of the virus into a cell. The SF viral stock used in transfection assays exemplified herein is believed to contain inhibitory media components which inhibit transfection as higher levels of viral stock are added. Viral stock free of such inhibitory components is preferred. Methods for purifying viral stock are well-known in the art.

A variety of cationic lipids is known in the art. Example structures of cationic lipids useful in this invention are provided in Table 1. Generally, any cationic lipid, either monovalent or polyvalent, can be used in the compositions and methods of this invention. Polyvalent cationic lipids are generally preferred. Cationic lipids include saturated and unsaturated alkyl and alicyclic ethers and esters of amines, amides or derivatives thereof. Straight-chain and branched alkyl and alkene groups of cationic lipids can contain from 1 to about 25 carbon atoms. Preferred straight-chain or branched alkyl or alkene groups have six or more carbon atoms. Alicyclic groups can contain from about 6 to 30 carbon atoms. Preferred alicyclic groups include cholesterol and other steroid groups. Cationic lipids can be prepared with a variety of counterions (anions) including among others: $Cl^-$, $Br^-$, $I^-$, $F^-$, acetate, trifluoroacetate, sulfate, nitrite, and nitrate.

A well-known cationic lipid is N-[1-(2,3-dioleoyloxy)propyl]-N,N,N-trimethylammonium chloride (DOTMA). See Felgner, P. L. et al. (1987) Proc. Natl. Acad. Sci. USA 84:7413–7417. DOTMA and the analogous diester DOTAP (1,2-bis(oleoyloxy)-3-3-(trimethylammonium)propane), see Table 1 for structures, are commercially available. Additional cationic lipids structurally related to DOTMA are described in U.S. Pat. No. 4,897,355, which is incorporated by reference in its entirety herein.

Another useful group of cationic lipids related to DOTMA and DOTAP are commonly called DORI-ethers or DORI-esters. DORI lipids differ from DOTMA and DOTAP in that one of the methyl groups of the trimethylammonium group is replaced with a hydroxyethyl group, see structure in Table 1. The DORI lipids are similar to the Rosenthal Inhibitor (RI) of phospholipase A (Rosenthal, A. F. and Geyer, R. P. (1960) J. Biol. Chem. 235:2202–2206). The oleoyl groups of DORI lipids can be replaced with other alkyl or alkene groups, such as palmitoyl or stearoyl groups. The hydroxyl group of the DORI-type lipids can be used as a site for further functionalization, for example for esterification to amines, like carboxyspermine.

Additional cationic lipids which can be employed in the compositions and methods of this invention include those described as useful for transfection of cells in PCT application WO 91/15501 published Oct. 17, 1991, Pinnaduwage, P. et al. (1989) Biochem. Biophys. Acta. 985:33–37; Rose, J. K. et al. (1991) BioTechniques 10:520–525; Ito, A et al. (1990) Biochem, Intern, 22:235–241.

Cationic sterol derivatives, like 3β[N-(N',N'-dimethylaminoethane)carbamoyl] cholesterol (DC-Chol) in which cholesterol is linked to a trialkyammonium group, see Table 1, can also be employed in the present invention. DC-Chol is reported to provide more efficient transfection and lower toxicity than DOTMA-containing liposomes for some cell lines. (Goa, X. and Huang, L. (1991) Biochem. Biophys. Res. Comm. 179:280–285.)

The polycationic lipid formed by conjugating polylysine to DOPE (Zhou, X. et al. (1991) Biochem. Biophys. Acta 1065:8–14), as well as other lipopolylysines, can also be employed in the methods and compositions of this invention.

Polycationic lipids containing carboxyspermine are also useful in the compositions and methods of this invention. Behr, J-P. et al. (1989) Proc. Natl. Acad. Sci. 82.:6982–6986 and EPO published application 304 111 (1990) describe carboxyspermine-containing cationic lipids including 5-carboxyspermylglycine dioctadecyl-amide (DOGS) and dipalmitoylphosphatidylethanolamine 5-carboxyspermylamide (DPPES). Additional cationic lipids can be obtained by replacing the octadecyl and palmitoyl groups of DOGS and DPPES, respectively, with other alkyl or alkene groups.

U.S. Pat. No. 5,334,761, issued Aug. 2, 1994, which is incorporated by reference in its entirety herein, describes cationic lipids of formula A which are useful in this invention:

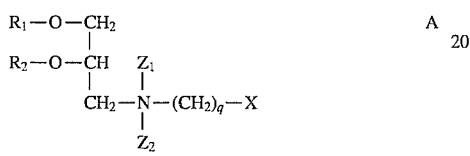

where $R_1$ and $R_2$ separately or together are $C_{1-23}$ alkyl or alkenyl or (—CO—$C_{1-23}$) alkyl or alkenyl, q is 1 to 6, $Z_1$ and $Z_2$, separately or together, are H or an unbranched alkyl group having one to six carbon atoms and where X can be a variety of groups including haloalkyl, alkylamines, alkyldiamines, alkyltriamines, aklytertamines, carboxyspermine and related amines, or polyamines including polylysine or polyarginine.

Compounds of formula A in which X is a nitrogen containing group such as:

—$(CH_2)_n NH_2$, where n=0–6 (X1)

—NH—$(CH_2)_m$—$NH_2$, wherein m=2–6 (X2);

—NH—$(CH_2)_3$—NH—$(CH_2)_4 NH_2$ (X3);

—NH—$(CH_2)_3$—NH—$(CH_2)_4$—NH—$(CH_2)_3$—$NH_2$ (X4);

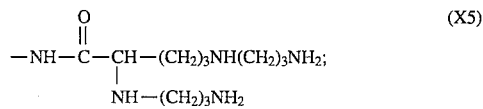

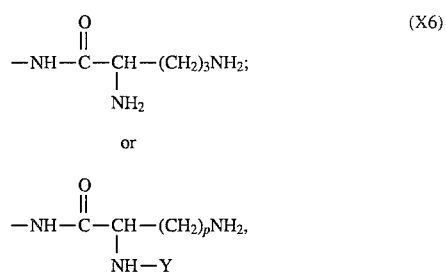

where p is 2–5 and Y is H or a group attached by an amide or alkyl amino group (X7) are particularly useful in the methods and compositions of the present invention for complexation to nucleic acids. Polycationic lipids, such as those of formula A where X is a spermine, like X5, are preferred.

In the transfection compositions of this invention cationic lipids can optionally be combined with non-cationic lipids, preferably neutral lipids, to form lipid aggregates that complex with nucleic acids. Neutral lipids useful in this invention include, among many others: lecithins; phosphotidyletahnolamine; phosphatidylethanolamines, such as DOPE (dioleoylphosphatidylethanolamine), POPE (palmitoyloleoylphosphatidylethanolamine) and distearoylphosphatidylethanolamine; phosphotidylcholine; phosphatidylcholines, such as DOPC (dioleoylphosphidylcholine), DPPC (dipalmitoylphosphatidylcholine) POPC (palmitoyloleoylphosphatidylcholine) and distearoylphosphatidylcholine; phosphatidylglycerol; phosphatidylglycerols, such as DOPG (dioleoylphosphatidylglycerol), DPPG (dipalmitoylphosphatidylglycerol), and distearoylphosphatidylglycerol; phosphatidylserine; phosphatidylserines, such as dioleoyl- or dipalmitoylphospatidylserine; diphosphatidylglycerols; fatty acid esters; glycerol esters; sphingolipids; cardolipin; cerebrosides; and ceramides; and mixtures thereof. Neutral lipids also include cholesterol and other 3βOH-sterols.

TABLE 1

Examples of Cationic Lipids

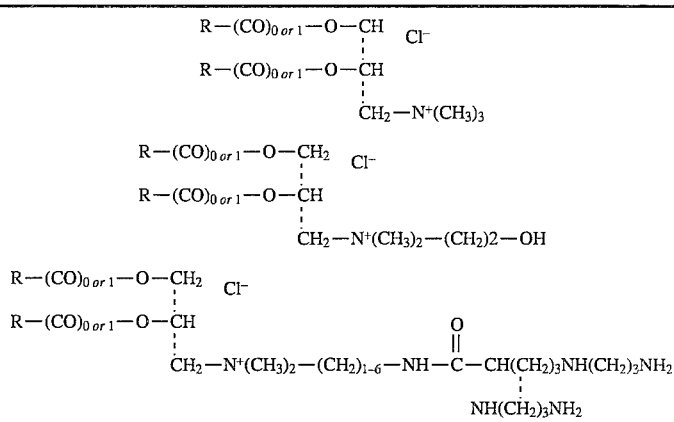

TABLE 1-continued

Examples of Cationic Lipids $$(R)_2-N-\overset{\overset{O}{\|}}{C}-CH_2-NH-\overset{\overset{O}{\|}}{C}-\underset{\underset{NH(CH_2)_3NH_2}{|}}{CH}(CH_2)_3NH(CH_2)_3NH_2$$

$$\begin{array}{l} R-\overset{\overset{O}{\|}}{C}-O-CH_2 \\ R-\overset{}{\underset{\underset{O}{\|}}{C}}-O-\overset{}{\underset{}{CH}} \\ \phantom{R-C-O-}CH_2-O-\overset{\overset{O}{\|}}{\underset{\underset{O_-}{|}}{P}}-O-CH_2-CH_2-NH-\overset{\overset{O}{\|}}{C}-\underset{\underset{NH(CH_2)_3NH_2}{|}}{CH}-(CH_2)_3NH(CH_2)_3NH_2 \end{array}$$

$$(CH3)-\overset{+}{N}H-(CH_2)_2-NH-\overset{\overset{O}{\|}}{C}\text{-[Cholesterol]}$$

Transfection efficiency of the methods of this invention can be further enhanced and the range of cell types to which these methods can be applied can be broadened by introducing 3βOH-sterols, such as cholesterol into the cell membrane of cells to be transfected.

SFV fuses in vitro with liposome membranes. These in vitro fusions have an absolute requirement for the presence of cholesterol or another 3βOH-sterol in the liposome. Kielian and Helenius (1984) supra; White and Helenius (1980) supra; Wahlberg et al. (1992) supra. In vivo infection by SFV also requires the presence of cholesterol in target cell membranes. Phalen and Kielian (1991) supra.

In the present method 3βOH-sterol can be introduced into the target cell membrane in a pre-treatment step by growing the cells in medium containing high concentrations of the sterol. As used herein, "high concentrations" of 3βOH-sterol or a "medium rich" in a 3βOH-sterol means a medium containing approximately 10 mg/L of said sterol. Alternatively, target cells can be pre-treated with liposomes containing the sterol and the sterol can be introduced into the cell membrane by a lipid fusion or lipid transfer process. Methods for producing liposomes containing 3βOH-sterols are well-known in the art. Methods for introducing a sterol or increasing the level of a sterol in cell membranes are also well-known in the art. Optimal fusion of SFV with cholesterol- containing liposomes is reported to be obtained at a ratio of cholesterol to phospholipid of 1:2 (Kielian and Helenius (1985) supra).

Pretreatment of cells to incorporate 3βOH-sterol such that the ratio of 3βOH-sterol to cell phospholipid is about 1:2 followed by treatment of the cells with a transfection composition of this invention comprising alphavirus will result in significant enhancement of transfection compared to transfection employing cationic lipid alone.

Improvement of the transfection methods of this invention can also be achieved by including 3βOH-sterols, such as cholesterol, in the cationic lipid aggregates in the transfection compositions of this invention.

Methods of this invention can also employ 3βOH-sterols in the transfecting composition. For example, transfecting compositions include, but are not limited to, those in which:

cationic lipids containing 3βOH-sterol are formed, complexed with nucleic acid and combined with virus or viral components;

cationic lipid aggregates, such as liposomes, containing 3βOH-sterol are formed, fused with an enveloped virus and the resulting virus-fused aggregates are complexed with nucleic acid;

cationic lipid, neutral lipid including 3βOH-sterol and virus or viral components are combined and subjected to treatments to form lipid aggregates and the resulting aggregate is complexed with nucleic acid; or cationic lipid, neutral lipid including 3βOH-sterol, virus or viral component and nucleic acid are combined and subjected to treatments to form lipid aggregates.

It will be readily apparent to those of ordinary skill in the art that a number of parameters are important for optimal transfection. These parameters include cationic lipid concentration, relative amounts of cationic and non-cationic lipid, the concentration of nucleic acid, the medium employed for transfection, the length of time the cells are incubated with transfection composition, the amount of virus or viral component employed, and the way in which the components of the transfection composition are combined into lipid aggregates. It may be necessary to optimize these parameters for each cell type to be transfected. Such optimization is routine employing the guidance provided herein and transfection assays as described in the Examples herein.

It will also be apparent to those of ordinary skill in the art that alternative methods, reagents, procedures and techniques other than those specifically detailed herein can be employed or readily adapted to produce the transfection compositions of this invention and practice the transfection methods of this invention. Such alternative methods, reagents, procedures and techniques are within the spirit and scope of this invention.

The transfection compositions and methods of this invention are further illustrated in the following non-limiting Examples. All abbreviations used herein are standard abbreviations in the art. Specific procedures not described in detail in the Examples are well-known in the art.

EXAMPLES

EXAMPLE 1

Cell Cultures and Plasmids

Standard tissue culture methods were employed. Baby hamster kidney (BHK-21) cells were grown in Dulbecco's-modified Eagle's medium (DMEM) containing 10% (v/v)

fetal bovine serum (FBS), 2 mM L-glutamine (gln), 0.1 mM MEM nonessential amino acids (NEAA), 100 U/ml penicillin (PEN) and 100 μg/ml streptomycin (STREP), hereafter DMEM complete.

Human primary fibroblasts (HPF) were isolated from neonatal foreskin tissue and prepared as follows. Rinsed, fresh tissue was exposed to 25 U/ml dispase (Collaborative Research) overnight at 4° C., separated into epidermis and dermis, and the minced dermis was digested 10 min at 37° C. in 0.25% trypsin, 1 mM EDTA. The reaction was stopped by a rinse and centrifugation in DMEM with 10% (v/v) FBS (PEN and STREP), in which the cells were also cultured. These cultures were used within the first five passages.

COS 7 and HeLa cells are grown in DMEM complete. CHO-K1 cells were cultured in EMEM with 2 mM proline, 5% (v/v) FBS, PEN and STREP. NIH 3T3 cells were cultures in DMEM with 10% (v/v) calf serum (PEN and STREP). Jurkat cells are cultured in RPMI 1640 with 10% FBS (PEN and STREP). PC 12 cells were cultured in DMEM with 5% (v/v) FBS and 10% heat-inactivated Horse serum (GIBCO BRL). Cells are maintained in a humidified incubator with a 5% $CO_2$ atmosphere at 37° C.

The plasmid vector pCMVβ is a commercially available (Clontech, Calif.) mammalian reporter vector containing the E. coli β-galactosidase (β-gal) gene under the control of the Cytomegalovirus promoter. See: MacGregor et al. (1989) Nucleic Acids Res. 17: 2365; Norton et al. (1985) Mol. and Cell Biol. 5:281; Alam (1990) Anal. Biochem. 188:245. Plasmid DNA was purified by standard cesium chloride methods.

EXAMPLE 2

Semliki Forrest Virus Preparation and Viral Treatments

Infectious Semliki Forest virus (SFV) particles containing modified SFV RNA lacking the subgenomic coding region for the viral structural proteins were employed in transfection experiments of Tables 3–6. The modified SFV RNA employed, pSFV1-tdt and pSFV3-lacZ, contained a tdt gene (terminal deoxynucleotidyl transferase) and a lacZ gene, respectively, under the control of the viral subgenomic promoter. Viral particles containing the modified SFV RNA were produced in BHK cells by an in vivo packaging system employing a packaging-deficient SFV helper plasmid, specifically helper 2, which encoded the viral structural proteins. See: Liljestrom and Garoff (1991) supra.

Viral particles were collected from BHK cell tissue culture grown in GMEM (10% (v/v) tryptase phosphate broth, 5% (v/v) FBS, 2 mM gln, 100 U/ml PEN and 100 μg/ml STREP) and frozen in the same medium. Untreated viral particles were obtained by thawing aliquots of frozen stock.

Inactive virus was obtained either by heating an aliquot of viral stock at 65° C. for 5 min. (heat-inactivated), by subjecting an aliquot of viral stock to 2 additional freeze-thaw cycles (freeze-thaw inactivated) or by exposing an aliquot of vital stock to UV light (30 Watt/253.7 nm) for 10 min (UV-inactivation).

Inactivation of the virus was assessed by subjecting modified SFV particles containing a lacZ gene under the control of the vital subgenomic promoter, pSFV3-lacZ (Liljestrom and Garoff (1991) supra) to the inactivating conditions and assaying for expression of β-galactosidase from the virus in infected BHK cells stained with 5-bromo-4-chloro-3-indolyl-β-δ-galactoside (X-gal).

The SFV stock solution employed in BHK cell and human primary fibroblast transfection assays is estimated to contain $10^7$ virus particles/ml. Vital titer was estimated by titration of vital stock on BHK cells. The titer of pSFV3-lacZ vital stock was estimated in BHK cells stained with X-gal. The titer of pSFV1-tdt was estimated by assessing cell toxicity after 30 hr of infection. The end point of dilution is the point when approximately 100% of the BHK cells are infected.

EXAMPLE 3

Comparison of Transfection Activity of Lipid Reagents

Cell lines were transfected with pCMVβgal using various lipid reagents "LIPOFECTAMINE", "LIPOFECTIN", "LIPOFECTACE", DOTAP or calcium phosphate to compare transfection activity of different cell lines.

Cationic lipid formulations "LIPOFECTIN", "LIPOFECTAMINE", "LIPOFECTACE" all commercially available (Gibco/BRL: Life Technologies, Inc., Gaithersburg, Md.), were employed in transfection assays. "LIPOFECTIN" is a 1:1(w/w) mixture of N[1-(2,3-dioleyloxy)propyl]-N,N,N-trimethylammonium chloride (DOTMA) and dioleoylphosphatidylethanolamine (DOPE). "LIPOFECTAMINE" is a 3:1 (w/w) mixture of the polycationic lipid, 2,3-dioleyloxy-N-[2(sperminecarboxamido)ethyl]-N,N-dimethyl-1-propanaminium trifluoroacetate (DOSPA), and DOPE. "LIPOFECTACE" (formerly called "TRANSFECTACE")is a 1:2.5 (w/w) mixture of the cationic lipid dimethyldioctadecylammonium bromide (DDAB) and DOPE.

In these comparative assays, cationic lipid formulations sold under the trademarks "Lipofectamine," "Lipofectin," and "Lipofaectace" "LIPOFECTAMINE", "LIPOFECTIN", "LIPOFECTACE" were used according to the manufacturer's (GIBCO/BRL) recommendations. Briefly, lipid and DNA were diluted separately into 25-μl aliquots of "OPTI-MEM" I Reduced-Serum Medium (without serum). The aliquots were gently mixed and incubated at room temperature for 15 to 45 min to form DNA-lipid complexes. The complexes were diluted with 250-μl transfection medium and the mixture was added to subconfluent cells in 24 mm well plate of 6-well tissue culture plates. The cells were rinsed with the same transfection medium prior to addition of complexes to cells. The cells were exposed to complexes for 6 to 24 hr under standard culture conditions and then were fed their normal growth medium. Antibiotics were not present during transfections. Transient assays were performed 24 hr after transfection. In each case, the amount of lipid was varied to determine an optimal lipid concentration for transfection. Results obtained with optimal lipid concentrations were compared in Table 2.

DOTAP (Boehringer-Mannheim) was used according to the manufacturer's recommendations. Calcium phosphate co-precipitation transfections were performed in medium containing 10% (v/v) calf serum, using the commercially available Calcium Phosphate Transfection System (GIBCO/BRL).

In situ staining was used to demonstrate β-gal expression (Sanes, J. R. et al. (1986) EMBO J 5:3133). Cells were rinsed with PBS, fixed for 5 min in 2% (v/v) formaldehyde, 0.2% glutaraldehyde in PBS, rinsed twice with PBS, and stained 2 h to overnight with 0.1% X-gal, 5 mM potassium ferricyanide, 5 mM potassium ferrocyanide, 2 mM $MgCl_2$ in PBS. Rinsed cells were photographed using a 10X objective on a Nikon inverted microscope with Hoffman optics. The percent of stained cells in transfected cultures was determined from counts of three fields for optimal lipid concentrations. The results of transfections of NIH 3T3, CHO-K1, BHK-21, PC 12, and human primary fibroblasts with pCMVβ with various cationic lipid treatments are presented in Table 2. Hard to transfect cell lines are those like HPF cells in which less than about 10% of the cells are transfected with "LIPOFECTAMINE" treatment.

TABLE 2

Transfection Activity Assessed as β-Gal Activity

| Transfection Agent | Percent Cells Transfected[1] Cell Type | | | | |
|---|---|---|---|---|---|
| | NIH 3T3 | CHO-K1 | BHK-21 | PC12 | HPF[2] |
| "LIPOFECT-AMINE" | ~80 ± 5 | ~92± | ~86 | ~30% | <5% |
| "LIPO-FECTIN" | 15 ± 5 | ND | ND | <5% | <1% |
| "LIPO-FECTACE" | 3 ± 1 | ND | ND | <5% | <1% |
| DOTAP | 6 ± 3 | ND | ND | <5% | <1% |
| CaPO$_4$ | 3 ± 3 | ND | ND | <5% | <1% |

[1]ND = not done
[2]HPF = Human Primary Fibroblast

EXAMPLE 4

Transfection Assays in BHK Cells Adding SFV

BHK cells were plated in 24-well tissue culture dishes (2×10$^4$ cells/well) and incubated overnight in DMEM complete. Growth medium was removed from cells and they were washed once with reduced-serum medium, "OPTI-MEM" I (Gibco/BRL: Life Technologies, Inc., Gaithersburg, Md.) and 250 µl of "OPTI-MEM" I was added to each well. For each well, a DNA solution containing 0.2 µg of plasmid DNA, e.g. pCMvβ plasmid DNA, and a cationic lipid solution containing 4 µg of "LIPOFECTAMINE" both in 25 µl of "OPTI-MEM" I were prepared. The DNA and cationic lipid solutions were mixed and incubated for 10–15 min at room temperature to allow the formation of DNA-cationic lipid complexes. Various amounts of treated and untreated virus were added to the DNA-lipid aggregate containing solutions which were then added to cells in individual wells. Cells were incubated (37° C., 5% CO$_2$) for 6 hrs, the transfecting solution was then removed and replaced with cell growth medium (DMEM complete).

Cells were incubated for an additional 24 hr., after which they were assayed for β-gal activity. Cells from individual wells were collected and suspended in 250 µl of a lysis buffer, 0.1 Tris-HCl (pH 8.0) containing 0.1% Triton X-100 and assayed for activity employing the method essentially as described in Sambrook et al. (1989) Molecular Cloning A Laboratory Manual, 2nd Ed., Cold Spring Harbor Laboratory Press, p. 16–66.

Similar transfection assays were performed using "LIPOFECTIN" (initial concentration 2 µg lipid/25 µl "OPTI-MEM" I) in combination with untreated and treated SFV.

Cationic lipid formulations "LIPOFECTIN" and "LIPOFECTAMINE", both commercially available (Gibco/BRL: Life Technologies, Inc., Gaithersburg, Md.), were employed in transfection assays. "LIPOFECTIN" is a 1:1 (w/w) mixture of N-[1-(2,3-dioleyloxy)propyl]-N,N,N-trimethylammonium chloride (DOTMA) and dioleoylphosphatidylethanolamine (DOPE). "LIPOFECTAMINE" is a 3:1 (w/w) mixture of the polycationic lipid, 2,3-dioleyloxy-N-[2(sperminecarboxamido)ethyl]-N,N-dimethyl-1-propanaminium trifluoroacetate (DOSPA), and DOPE.

Results of transfection assays in BHK cells using "LIPOFECTAMINE" are given in Tables 2–4. Data in Tables 2–4, the average of 2 replicates, show the effect of addition of increasing amounts of untreated and treated SPY particles (in µl of SFV stock solution) on transfection of pCMVβgal complexed with "LIPOFECTAMINE" as measured by β-gal activity (O.D.$_{420\ nm}$).

Table 3 shows the enhancement of transfection of plasmid DNA complexed to cationic lipid by untreated SFV particles. An 11.3-fold enhancement over transfection in the absence of virus is observed on addition of 3 µl of vital stock. The decrease in β-gal activity with increasing levels of SFV stock (10 and 30 µl) is believed to reflect inhibition of transfection by proteinaceous inhibitors or medium components (e.g. serum) in the cell culture medium in which the stock was prepared.

Tables 4 and 5 show the enhancement of transfection of plasmid DNA complexed with cationic lipid by heat inactivated and freeze-thaw inactivated virus, respectively. Enhancement of transfection is similar to that observed with untreated SFV. A 15.5-fold and 10.9-fold enhancement is observed with 3 µl levels of heat-inactivated and freeze-thaw inactivated virus, respectively. A similar pattern of enhancement of transfection by SFV particles was observed when "LIPOFECTIN" was employed as the cationic lipid in transfections.

TABLE 3

Effect of untreated SFV particles on transfection of BHK cells.

| SFV (µl) | β-gal Activity O.D.$_{420\ nm}$ | Enhancement |
|---|---|---|
| 0 | 0.047 | — |
| 1 | 0.410 | 7.1 |
| 3 | 0.529 | 11.3 |
| 10 | 0.150 | 3.1 |
| 30 | 0.058 | 1.2 |
| Cells Only | 0.011 | — |

TABLE 4

Effect of heat-inactivated SFV particles on transfection of BHK cells.

| SFV (µl) | β-gal Activity O.D.$_{420\ nm}$ | Enhancement |
|---|---|---|
| 0 | 0.038 | — |
| 1 | 0.495 | 13.0 |
| 3 | 0.591 | 15.5 |
| 10 | 0.134 | 3.5 |
| 30 | 0.090 | 2.3 |
| Cells Only | 0.011 | — |

TABLE 5

Effect of freeze-thaw inactivated SFV particles on transfection of BHK cells.

| SFV (µl) | β-gal Activity O.D.$_{420\ nm}$ | Enhancement |
|---|---|---|
| 0 | 0.028 | — |
| 1 | 0.362 | 12.9 |
| 3 | 0.307 | 10.9 |
| 10 | 0.183 | 6.5 |
| 30 | 0.089 | 3.1 |
| Cells Only | 0.011 | — |

EXAMPLE 5

Transfection Assays in Human Primary Fibroblast (HPF) cells Adding SFV

HPF cells were plated in 24-well tissue culture dishes ($4 \times 10^4$ cells/ 24 well plate) and incubated overnight in DMEM complete. Growth medium was removed from cells and they were washed once with reduced-serum medium, "OPTI-MEM" I and 250 μl of "OPTI-MEM" I was added to each well. For each well, a DNA solution containing 0.2 μg of pCMvβ plasmid DNA and a cationic lipid solution containing "LIPOFECTAMINE" (4 μg lipid/25 μl "OPTI-MEM" I) are prepared. The DNA solution and cationic lipid solution were mixed and incubated for 10–15 min at room temperature to allow the formation of DNA-cationic lipid aggregates. Varying amounts (as indicated in μl of viral stock) of treated and untreated virus were added to the DNA-lipid aggregate containing solutions which were then added to cells in individual wells. Cells were incubated (37° C., 5% $CO_2$) for 6 hr, the transfecting solution was then removed and replaced with cell growth medium (DMEM complete). Cells were incubated for an additional 24 hr, after which they were assayed for β-gal activity. Cells from individual wells were collected and suspended in 250 μl of a lysis buffer, 0.1 Tris-HCl (pH 8.0) containing 0.1% Triton X-100 and assayed for β-gal activity employing the method essentially as described in Sambrook et al. (1989) supra.

Results of transfection assays in HFP cells with SFV pSFV1-tdt particles are given in Table 6. Data in Table 6 are not normalized for protein and are the average of 2 replicates. Table 6 compares transfection activity for addition of virus particles (pSVF1-tdt) in the presence and absence of cationic lipid, "LIPOFECTAMINE", and shows the effect of addition of increasing amounts of untreated and treated (UV-inactivated and heat-inactivated) SFV particles (in μl of SPY stock solution) on transfection of pCMVβgal complexed with lipid as measured by β-gal activity ($O.D._{420\ nm}$).

Untreated pSVF1-tdt as well as heat- and UV-treated pSFV1-tdt significantly enhance transfection of HPF cells by cationic lipid/DNA complexes. UV-inactivated virus appears to give approximately a 2-fold enhancement over untreated and heat-inactivated virus. Addition of UV-inactivated virus to cells treated with cationic lipid and DNA results in up to a 25-fold enhancement in transfection activity (β-gal activity). As noted above, HPF is a "hard to transfect" cell line, in which less than about 5% of the cells are transfected in the presence of a cationic lipid such as "LIPOFECTAMINE". Results in Table 6 confirm that only low levels of transfection of HPF cells are observed in the presence of "LIPOFECTAMINE" using this assay system. Under the conditions of these experiments, pSVF1-tdt in the absence of cationic lipids does not cause significant transfection of HPF cells. Thus, the combination of SFV viral components and cationic lipid results in a synergistic enhancement of transfection in HPF cells.

TABLE 6

Results of Transfection Assays in Human Primary Fibroblasts with "LIPOFECTAMINE" and Semliki Forest Virus

| Cell Treatment | Virus (μl) | β-Gal Assay $O.D._{420\ nm}$ | Fold Enhancement |
| --- | --- | --- | --- |
| pSFV1-tdt + lipid pCMVβgal | 0 | 0.013 | — |
| | 2.5 | 0.089 | 6.8 |
| | 5 | 0.195 | 15.0 |
| | 10 | 0.193 | 14.8 |
| | 15 | 0.203 | 15.6 |
| | 20 | 0.189 | 14.5 |
| heat-inactive pSFV1-tdt + lipid pCMVβgal | 0 | 0.017 | — |
| | 2.5 | 0.101 | 5.9 |
| | 5 | 0.092 | 5.4 |
| | 10 | 0.152 | 8.9 |
| | 15 | 0.206 | 12.1 |
| | 20 | 0.174 | 10.2 |
| UV-inactive pSFV1-tdt + lipid pCMVβgal | 0 | 0.011 | — |
| | 2.5 | 0.104 | 9.5 |
| | 5 | 0.113 | 10.3 |
| | 10 | 0.208 | 18.9 |
| | 15 | 0.255 | 23.2 |
| | 20 | 0.277 | 25.2 |
| pSFV1-tdt alone no lipid pCMVβgal | 0 | 0.017 | — |
| | 2.5 | 0.011 | 0.7 |
| | 5 | 0.017 | 1.0 |
| | 10 | 0.018 | 1.1 |
| | 15 | 0.010 | 0.6 |
| | 20 | 0.012 | 0.7 |

EXAMPLE 6

Transfection of BHK-21 Cells Employing Cationic Liposomes incorporating SFV.

BHK-21 cells were plated in 24-well tissue culture dishes ($2 \times 10^4$ cells/well) and incubated overnight in DMEM complete. Growth medium was removed from cells and they were washed once with "OPTI-MEM" I and 250 μl of "OPTI-MEM" I was added to each well. Transfection compositions containing "LIPOFECTAMINE" and inactivated (heat- or Uv-inactivated) SFV (pSFV1-tdt) were prepared as follows:

A set of liposome solutions (100 μl each) which each contained 50 μl of a 2 mg/ml solution of "LIPOFECTAMINE" in water and either 1, 3, 10, or 30 μl of viral stock (inactivated) with enough water added to each solution to make up to 100 μl. A no-virus control containing 50 μl of 2 mg/ml "LIPOFECTAMINE" solution, 10 ml of medium (that used to prepare viral stock) and 40 μl of water was also prepared. The final lipid concentration in these solutions was 1 mg/ml. The inactivated viral stock was added last to the solutions and all solutions, including the no-virus control, were subjected to freeze/thaw cycles (−70° C./37° C.) to induce formation of cationic liposome incorporating SFV. For each well, 25 μl of a DNA solution containing 0.2 μg of pCMVβ in "OPTI-MEM" I and a 25 μl solution containing varying amount of the liposome solution were mixed and incubated for 10–15 min at room temperature to allow complex formation. The complex containing solutions were then added to cells and cells were incubated (37° C., 5% $CO_2$) for 6 hrs. The transfecting solution was then removed and replaced with cell growth medium (DMEM complete). Cells were incubated for an additional 24 hr, after which they were assayed for β-gal activity, as described in Example 3. Exemplary results of this transfection assay are presented in Table 7. Data in Table 7 are the average of two replicates and present O.D. measurements as a function of increasing amounts of liposome solution (μl) added to transfection solutions. Data for 10 μl and 30 μl additions of heat- and UV-inactivated SFV(p-SFV1-tdt), the no-virus control and cells only control are provided. Data in Table 7 are not normalized for protein content. The amount of DNA, the total amount of lipid, the relative amounts of cationic and neutral lipid and freeze-thaw treatment were not optimized in these assays.

Even though the liposome preparation has not been optimized for these transfection assays, the data in Table 7 show a significant enhancement of transfection (as expression of β-gal) in cells treated with the combination of cationic lipid and SFV over those treated with cationic lipids alone.

TABLE 7

Tranfection of BHK cells with Cationic Liposomes incorporating SFV

| Transfection Treatment | Liposome solution (μl) | β-Gal Assay O.D.$_{420\ nm}$ |
|---|---|---|
| 10 μl heat-inactivated SFV + Lipid | 1 | 0.003 |
| | 3 | 0.193 |
| | 10 | 0.152 |
| | 30 | 0.003 |
| 30 μl heat-inactivated SFV + Lipid | 1 | 0.004 |
| | 3 | 0.521 |
| | 10 | 0.182 |
| | 30 | 0.013 |
| 10 μl UV-inactivated SFV + Lipid | 1 | 0.003 |
| | 3 | 0.551 |
| | 10 | 0.331 |
| | 30 | 0.037 |
| 30 μl UV-inactivated SFV + Lipid pCMVβgal | 1 | 0.004 |
| | 3 | 0.437 |
| | 10 | 0.197 |
| | 30 | 0.012 |
| No Virus Lipid Control | 1 | 0.007 |
| | 3 | 0.107 |
| | 10 | 0.003 |
| | 30 | 0.002 |
| Cells Only Control | | 0.002 |

EXAMPLE 7

Transfection of Human Fibroblast Cells Employing Cationic Liposomes Incorporating Fusion Peptides from Enveloped Viruses.

Peptides from Influenza virus hemagglutinin (E5 amphiphilic peptide) and Vesicular Stomatitis virus glycoprotein (VSV G protein) were synthesized using standard Fmoc peptide synthesis. See: Kamata, H. et al. (1994) Nucleic Acids Res. 22:536–537 (peptide E5); Schlegel, R. and M. Wade (1985) J. Virol. 53:319–323 (peptide KFT (6)); and Stewart et al. (1984) *Solid Phase Peptide Synthesis*, Pierce Chemical Company, Rockford, Ill. These peptides had been identified as active in mediating membrane fusion during infection by their respective viruses.

Human primary fibroblast (HPF) cells were plated in 24-well tissue culture dishes (8×10$^4$ to 1×10$^5$ cells per well) and incubated overnight in DMEM complete. Growth medium was removed from cells and they were washed once with serum-free DMEM and 250 μl DMEM was added to each well. Transfection compositions containing "LIPOFECTAMINE" (Gibco/BRL: Life Technologies, Inc., Gaithersburg, Md.), DNA and peptides were prepared as follows:

Peptides were dissolved at 300× final concentration (see table) in water. For each well, 25 μl of a DNA solution containing 0.2 μg pCMVβ in "OPTI-MEM" I (Gibco/BRL: Life Technologies, Inc., Gaithersburg, Md.) and a 25 μl solution containing varying amounts of the liposome solution were mixed and incubated for 15 min at room temperature to allow complex formation. One microliter of peptide solution was then added to the complex containing solution, after which the whole complex containing solution was added to the cells. Cells were incubated (37° C., 5% CO$_2$) for 6 hrs. one milliliter of cell growth medium (DMEM complete) was added, and the cells were incubated for an additional 24 hr. Cells were harvested and assayed for β-gal activity, as described in Example 3, except that the amount of β-gal enzyme present was determined by comparing OD measurements with those of a standard curve. Exemplary results of this transfection assay are presented in Tables 8 and 9. Data are single determinations.

Data in Tables 8 and 9 are not normalized for protein content. The amount of lipid solution (2 μl for mixtures with peptides) and DNA (0.2 μg) had been optimized in previous assays. The amount of peptide was not optimized.

Even though the amount of peptide added to the liposome-DNA complexes has not been optimized for these transfection assays, the data in Tables 8 and 9 show a significant enhancement of transfection (as expression of β-gal) in cells treated with the combination of cationic lipid, DNA and peptide over those treated with cationic lipid and DNA alone.

TABLE 8

Transfection of human fibroblasts (HPF) with pCMVβ DNA using "LIPOFECTAMINE" and viral fusion peptides from influenza hemagglutinin and vesicular stomatitis virus (VSV) G protein.

| "LIPOFECTAMINE" solution (μl) | Influenza peptide (μM) | VSV peptide (μM) | ng β-galactosidase |
|---|---|---|---|
| 2 | 0 | 0 | 7 |
| 3 | 0 | 0 | 21 |
| 2 | 1 | 0.1 | 57 |
| 2 | 1 | 1 | 61 |
| 2 | 3 | 0.1 | 43 |
| 2 | 3 | 1 | 25 |
| 2 | 10 | 0.1 | 84 |
| 2 | 10 | 1 | 52 |

TABLE 9

Transfection of human fibroblasts (HPF) with pCMVβ DNA using "LIPOFECTAMINE" and viral fusion peptides from influenza hemagglutinin and vesicular stomatitis virus (VSV) G protein.

| "LIPOFECTAMINE" solution (μl) | Influenza peptide (μM) | VSV peptide (μM) | ng β-galactosidase |
|---|---|---|---|
| 2 | 0 | 0 | 35 |
| 2 | 0.01 | 0.01 | 92 |
| 2 | 0.1 | 0.1 | 94 |
| 2 | 1 | 1 | 96 |
| 2 | 2 | 2 | 72 |
| 2 | 5 | 5 | 108 |
| 2 | 10 | 10 | 46 |

I claim:

1. A composition for transfecting a eukaryotic cell wherein said composition comprises a nucleic acid, a cationic lipid composition selected from the group consisting of a 3:1 (w/w) mixture of the polycationic lipid, 2,3-dioleyloxy-N-[2(sperminecarboxamido)ethyl]-N,N-dimethyl-1-propanaminiumtrifluoroacetate and dioleoylphosphatidylethanolamine, and a 1:1 (w/w) mixture of N-[1-(2,3-dioleyloxy)propyl]-N,N,N-trimethylammoniumchloride and dioleoylphosphatidylethanolamine and a viral agent which enhances transfection two-fold or more by said cationic lipid composition, which viral agent is an alphavirus or a component of an alphavirus and wherein said nucleic acid is not a nucleic acid of said viral agent.

2. The transfection composition according to claim 1 wherein said cationic lipid composition is a 3:1 (w/w) mixture of the polycationic lipid, 2,3-dioleyloxy-N-[2(sperminecarboxamido)ethyl]-N,N-dimethyl-1-propanaminiumtrifluoroacetate and dioleoylphosphatidylethanolamine.

3. The transfection composition according to claim 1 wherein said cationic lipid composition is a 1:1(w/w) mixture of N-[1-(2,3-dioleyloxy)propyl]-N,N,N-trimethylammoniumchloride and dioleoylphosphatidylethanolamine.

4. The transfection composition of claim 1 wherein said alphavirus is a Semliki Forest virus or a Sindbis virus.

5. The transfection composition of claim 4 wherein said alphavirus is a Semliki Forest virus.

6. The transfection composition of claim 5 wherein said alphavirus is an inactive Semliki Forest virus.

7. The transfection composition of claim 6 wherein said Semliki Forest virus is a replication-deficient virus.

8. The transfection composition of claim 5 wherein said vital agent comprises a spike glycoprotein of Semliki Forest virus.

9. The transfection composition of claim 5 wherein said viral agent is a multimer of a spike glycoprotein of Semliki Forest virus.

10. The transfection composition of claim 5 wherein said vital agent is a peptide of a spike glycoprotein of Semliki Forest virus.

11. The transfection composition of claim 6 wherein the alphavirus is a heat-inactivated Semliki Forest virus.

12. The transfection composition of claim 1 wherein said alphavirus is an inactive alphavirus.

13. The transfection composition of claim 1 wherein said cationic lipid composition is formed into a cationic liposome or vesicle.

14. The transfection composition of claim 13 wherein said viral agent is incorporated into said cationic liposome or vesicle.

15. The transfection composition of claim 13 wherein said cationic lipid composition is fused with said viral agent.

16. The transfection composition of claim 1 wherein said viral agent is a Semliki Forest virus spike glycoprotein.

17. The transfection composition of claim 13 wherein said liposome or vesicle further comprises a 3β-OH sterol.

18. A method for transfecting a eukaryotic cell with a nucleic acid which comprises contacting said cell with the transfection composition of claim 1.

19. The method of claim 18 wherein said viral agent in said transfection composition is a Semliki Forest virus.

20. The method of claim 18 wherein said viral agent in said transfection composition is an inactive Semliki Forest virus.

21. The method of claim 18 wherein said vital agent in said transfection composition is a spike glycoprotein of a Semliki Forest virus.

22. The method of claim 18 wherein the cationic lipid composition in said transfection composition is a 3:1 (w/w) mixture of the polycationic lipid, 2,3-dioleyloxy-N-[2(sperminecarboxamido)ethyl]-N,N-dimethyl-1-propanaminiumtrifluoroacetate and dioleoylphosphatidylethanolamine.

23. The method of claim 18 wherein the cationic lipid composition of said transfection composition is a 1:1(w/w) mixture of N-[1- (2,3-dioleyloxy)propyl]-N,N,N-trimethylammoniumchloride and dioleoylphosphatidylethanolamine.

24. The method of claim 18 wherein said cationic lipid composition in said transfection composition is formed into a cationic liposome or vesicle.

25. The method of claim 24 wherein said vital agent of said transfection composition is incorporated into said cationic liposome or vesicle.

26. The method of claim 24 wherein said cationic lipid composition of said transfection composition is fused with said vital agent.

27. The method of claim 25, wherein said cationic liposome or vesicle further comprises a 3β-OH sterol.

28. The method of claim 18 which further comprises the step of introducing a 3β-OH sterol into the cell membrane of said eukaryotic cell prior to or simultaneously with contacting said cell with said transfection composition.

29. The method of claim 28 wherein said 3β-OH sterol is cholesterol.

30. The method of claim 28 wherein said 3β-OH sterol is introduced into the cell membrane of said eukaryotic cell by lipid fusion or exchange.

31. The method of claim 28 wherein said 3β-OH sterol is introduced into the cell membrane of said eukaryotic cell by growing or incubating said cells in a medium rich in said 3β-OH sterol.

32. The method of claim 18 wherein said eukaryotic cell is a suspension cell.

33. The method of claim 18 wherein said eukaryotic cell is an animal cell.

34. The method of claim 18 wherein said eukaryotic cell is selected from the group consisting of animal primary cells and animal embryo stem line cells.

35. The method of claim 18 wherein said eukaryotic cell is selected from the group consisting of human fibroblasts, keratinocytes and macrophages.

36. The transfection composition of claim 1 wherein said component of an alphavirus is a spike glycoprotein.

* * * * *

UNITED STATES PATENT AND TRADEMARK OFFICE
CERTIFICATE OF CORRECTION

PATENT NO. : 5,578,475
DATED : November 26, 1996
INVENTOR(S) : Jessee

It is certified that error appears in the above-indentified patent and that said Letters Patent is hereby corrected as shown below:

At column 15, line 59, "vital" should read --viral--.

At column 16, line 3, "Vital" should read --Viral--.

At column 16, line 4, "vital" should read --viral--.

At column 17, line 54, "16-66" should read --16.66--.

At column 18, line 4, "SPY" should read --SFV--.

At column 19, line 21, "vital" should read --viral--.

At column 19, line 46, "SPY" should read --SFV--.

UNITED STATES PATENT AND TRADEMARK OFFICE
CERTIFICATE OF CORRECTION

PATENT NO. : 5,578,475
DATED : November 26, 1996
INVENTOR(S) : Jessee

It is certified that error appears in the above-indentified patent and that said Letters Patent is hereby corrected as shown below:

At column 20, line 43, "Uv-inactivated)" should read --UV-inactivated)--.

At column 20, line 47, "vital" should read --viral--.

At column 20, line 53, "vital" should read --viral--.

At column 23, line 29, "vital" should read --viral--.

At column 23, line 35, "vital" should read --viral--.

At column 24, line 6, "vital" should read --viral--.

At column 24, line 21, "vital" should read --viral--.

At column 24, line 26, "vital" should read --viral--.

Signed and Sealed this

Fourth Day of March, 1997

Attest:

BRUCE LEHMAN

Attesting Officer

Commissioner of Patents and Trademarks